US007372055B2

(12) United States Patent
Harter, Jr. et al.

(10) Patent No.: US 7,372,055 B2
(45) Date of Patent: May 13, 2008

(54) NIGHT VISION INFRARED ILLUMINATOR

(75) Inventors: Joseph E. Harter, Jr., Kokomo, IN (US); Gregory K. Scharenbroch, Kokomo, IN (US); Siddharth S. Rege, Kokomo, IN (US)

(73) Assignee: Delphi Technologies, Inc., Troy, MI (US)

( * ) Notice: Subject to any disclaimer, the term of this patent is extended or adjusted under 35 U.S.C. 154(b) by 319 days.

(21) Appl. No.: 11/171,069

(22) Filed: Jun. 30, 2005

(65) Prior Publication Data

US 2007/0008735 A1 Jan. 11, 2007

(51) Int. Cl.
*A61N 5/06* (2006.01)
*G01J 3/10* (2006.01)
*H05G 2/00* (2006.01)

(52) U.S. Cl. .................... 250/504 R; 315/83; 315/325; 315/77; 315/324; 315/82; 362/227; 362/290; 362/291; 362/199; 362/507; 362/519; 362/538; 362/510

(58) Field of Classification Search ............ 250/504 R; 362/227, 290, 291, 299, 308, 310, 346, 507, 362/517, 519, 538, 510; 315/82, 83, 325, 315/77, 324
See application file for complete search history.

(56) References Cited

U.S. PATENT DOCUMENTS 5,977,694 A * 11/1999 McGuire .................... 313/110
6,650,058 B1 * 11/2003 Wang .......................... 315/82
2002/0171345 A1 11/2002 Golz et al.

FOREIGN PATENT DOCUMENTS

EP 1 258 674 11/2002
JP 09288908 11/1997
JP 2000235803 8/2000

OTHER PUBLICATIONS

Edmund Scientific Company, 1999 Optics and Optical Instruments Catalog, "Hot/Cold Mirrors," p. 84 and cover sheet.
European Search Report dated Sep. 15, 2006.

* cited by examiner

*Primary Examiner*—Jack Berman
*Assistant Examiner*—Meenakshi S Sahu
(74) *Attorney, Agent, or Firm*—Jimmy L. Funke

(57) ABSTRACT

An illuminator assembly is provided for supplying night vision illumination. The assembly includes a support housing and an infrared illumination source. An infrared reflector receives the radiation emitted from the infrared illumination source and reflects the infrared radiation in a first substantially collimated field of view and transmits visible light therethrough. A visible light reflector is located behind the infrared reflective mirror for receiving visible light transmitted through the infrared reflector and reflecting scattering the visible light in a second field of view.

23 Claims, 2 Drawing Sheets

NIGHT VISION INFRARED ILLUMINATOR

TECHNICAL FIELD

The present invention generally relates to night vision illumination and, more particularly, relates to an infrared illuminator, particularly for use in a night vision system.

BACKGROUND OF THE INVENTION

Night vision systems generally operate in the near infrared (IR) illumination range employing artificial illumination source(s) to illuminate a field of view. It has been proposed to employ night vision systems on automotive systems that illuminate the road scene in front of the vehicle with infrared radiation. The infrared illumination may illuminate a field of view well beyond the visible light illumination achieved with conventional vehicle headlights, without blinding passengers in oncoming traffic.

In conventional infrared light illumination systems, large power-consuming and inefficient illumination sources are typically employed to provide sufficient illumination for imaging devices to capture the forward road scene. The conventional illumination source typically includes a filament lamp which requires several hundred watts of power to provide the necessary illumination to cover a desired field of view with a range that extends up to one hundred fifty meters (150 m). Typically, expensive thermal management techniques are generally needed to ensure proper operation of the illumination sources in conventional illuminator assemblies.

In many night vision systems, only the infrared portion of the electromagnetic energy spectrum is used for the illumination of a desired field of view. The energy outside of the infrared spectrum, including the visible light energy, is generally discarded. Additionally, many night vision systems generally employ thermal energy management techniques, which add size and expense to the overall illuminator package. Thus, conventional night vision illuminators are generally energy inefficient and costly.

It is therefore desirable to provide for an infrared illuminator that is energy efficient and cost affordable. In particular, it is desirable to provide for an infrared illuminator that efficiently illuminates infrared radiation from a vehicle to enable night vision.

SUMMARY OF THE INVENTION

In accordance with the teachings of the present invention, an infrared illuminator assembly is provided for supplying night vision illumination. The illuminator assembly includes a support housing and an infrared illumination source. An infrared reflector is arranged to receive infrared radiation emitted from the infrared illumination source. The infrared reflector reflects infrared radiation in a first field of view and transmits visible light therethrough. A visible light reflector is located behind the infrared reflector for receiving the visible light transmitted through the infrared reflector. The visible light is reflected from the visible light reflector in a second field of view. Accordingly, infrared and visible light energy is illuminated in corresponding fields of view.

These and other features, advantages and objects of the present invention will be further understood and appreciated by those skilled in the art by reference to the following specification, claims and appended drawings.

BRIEF DESCRIPTION OF THE DRAWINGS

The present invention will now be described, by way of example, with reference to the accompanying drawings, in which.

DESCRIPTION OF THE PREFERRED EMBODIMENTS

Figure 1:
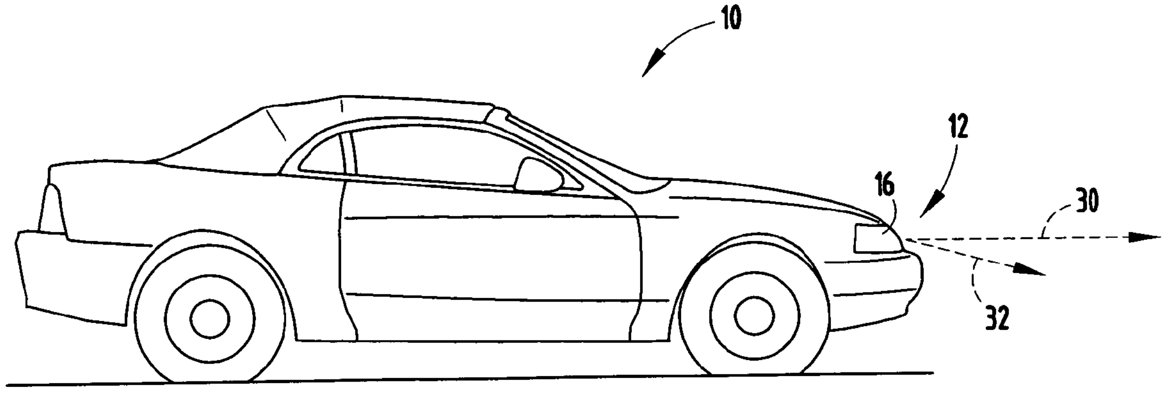
FIG. 1 is a side view of a vehicle employing a night vision infrared illuminator assembly.
Figure 3:
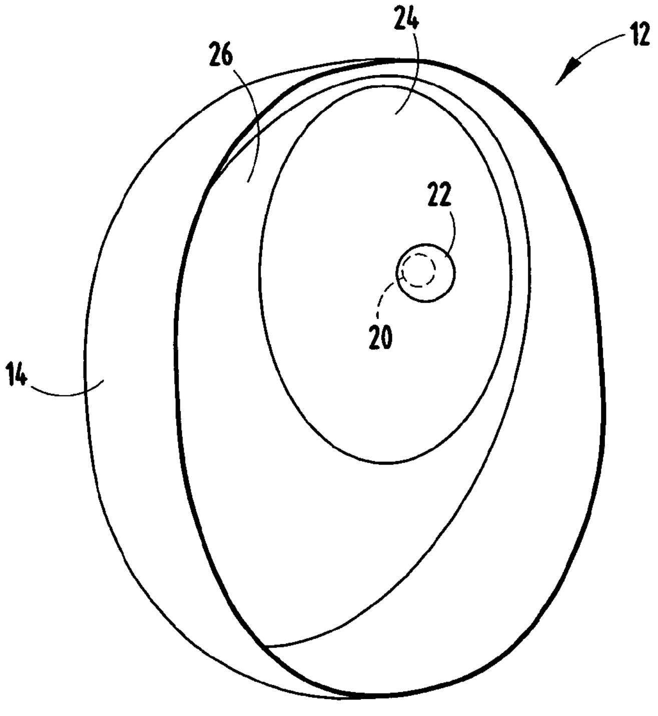
FIG. 3 is an enlarged front perspective view of the infrared illuminator assembly shown in FIG. 2 with the front lens omitted.
Figure 2:
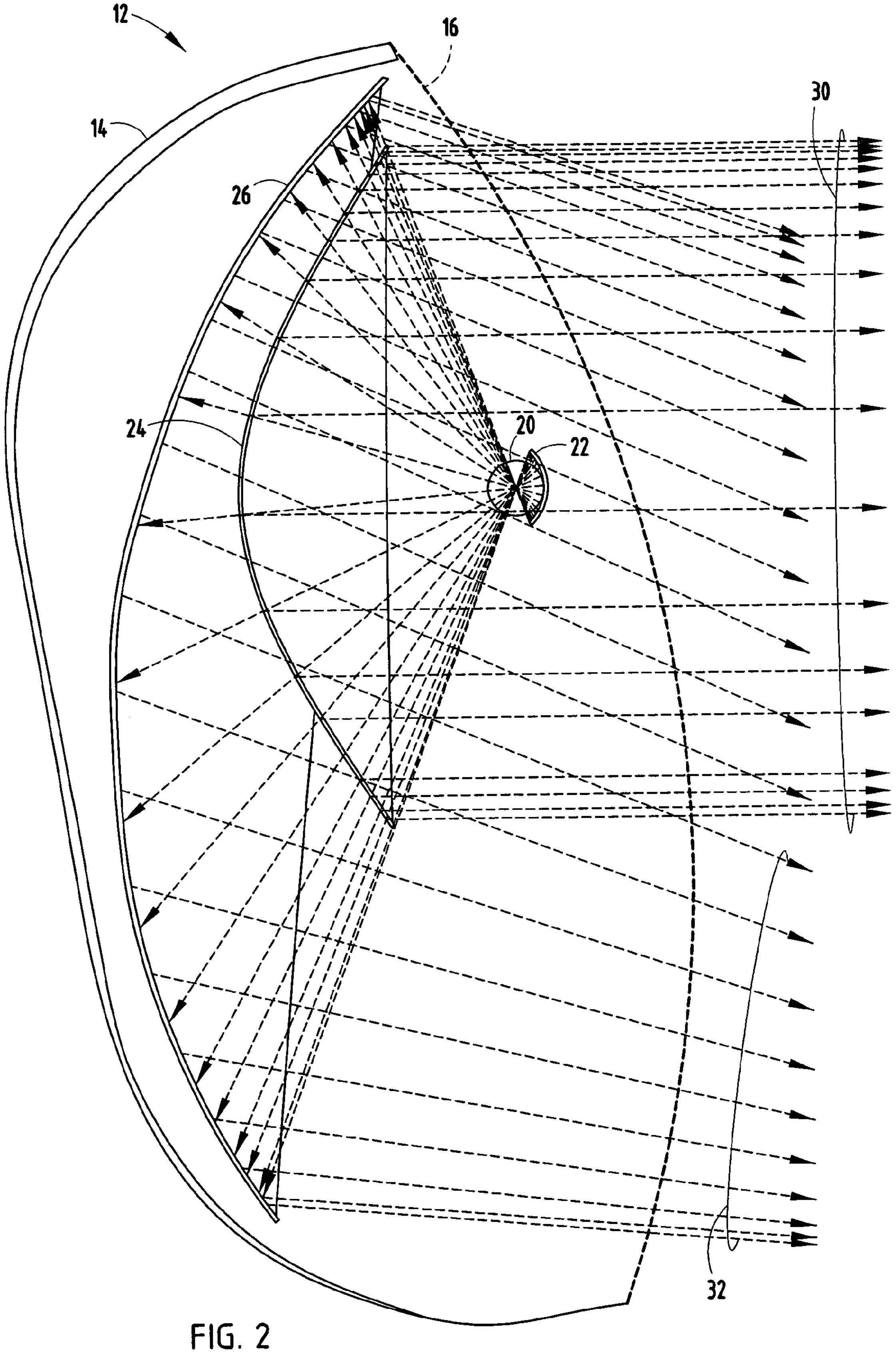
FIG. 2 is an enlarged side view of the infrared illuminator assembly according to one embodiment of the present invention.

Referring to FIG. 1, a vehicle is generally shown indicated by reference numeral 10 employing a night vision infrared (IR) illuminator assembly 12, according to one embodiment of the present invention. The night vision IR illuminator assembly 12 provides nighttime infrared (IR) illumination in a substantially collimated first field of view beam 30 forward of the vehicle 10. The illuminator assembly 12 also provides visible light illumination in a non-collimated (scattered) second field of view (beam) 32. The illuminator assembly 12 offers enhanced efficiency IR illumination which may be captured by a video imaging camera or other vision recognition or recording device to enable viewing of the images on a display by the driver of the vehicle. The illuminator assembly also recycles visible light for advantageous use seen directed onto the roadway forward of vehicle 10, according to one embodiment.

The IR illumination beam 30 includes electromagnetic radiation in the infrared and near infrared electromagnetic spectrum generally defined as energy radiation having a wavelength of $7\times10^{-7}$-$1\times10^{-3}$ meters (i.e., frequency of $3\times10^{11}$-$4\times10^{14}$ hertz). The IR radiation 30 is generally thermal energy that is unviewable to the naked eye. The visible light 32 is energy radiation that is visible to a human eye and generally is defined having a wavelength in the range of $4\times10^{-7}$-$7\times10^{-7}$ meters (i.e., frequency of $4\times10^{14}$-$7.5\times10^{14}$ hertz).

The vehicle 10 is generally shown employing a single night vision IR illuminator assembly 12, according to one embodiment. However, it should be appreciated that one or more IR illuminator assemblies 12 may be employed onboard any vehicle (e.g., car, truck, boat, aircraft, etc.). Additionally, the IR illuminator assembly 12 may be employed in other applications on or off a vehicle, including portable night vision systems.

The night vision IR illuminator assembly 12 generally includes a housing 14 supporting and enclosing the illuminator components. Housing 14 generally has side and rear walls and a clear light transmissive front lens 16. The front lens 16 freely transmits IR and visible light energy therethrough. Housing 14 may include a conventional vehicle headlamp housing for mounting on the front of the vehicle 10, according to the embodiment shown. However, it should be appreciated that the illuminator assembly 12 may be otherwise housed and/or located elsewhere on vehicle 10.

The illuminator assembly 12 includes an IR illumination source 20 mounted to housing 14 for primarily generating IR and near IR illumination, according to one embodiment. An optical reflector 22 is located forward of source 20 and has a rearward facing reflective surface for reflecting IR and visible light energy rearward. According to one embodiment, source 20 and reflector 22 generates and directs the energy in a cone shape having a field of view angle of about one hundred forty degrees to one hundred sixty degrees (140° to 160°). The IR illumination source 20 may include a conventional commercially available off-the-shelf illumination source. The amount of IR and visible light generated by source 20 may vary, depending on the source 20.

According to one embodiment, the illumination source 20 may include a filament bulb for generating IR radiation. It should be appreciated that commercially available infrared illumination sources, such as filament bulbs, generate infrared radiation in addition to energy radiation outside of the infrared energy spectrum, including visible light radiation. Hence, conventional infrared radiation bulbs are inefficient in that energy outside of the infrared radiation spectrum is also generated. One example of a filament type bulb is a 12-volt, 130 watt bulb, sold as part number 2763, commercially available from KC Hilites.

The illuminator assembly 12 includes a visible light transmissive/IR reflector (mirror) 24 mounted in housing 14 positioned to receive the infrared radiation emitted from illumination source 20, including energy reflected rearward by reflector 22. The IR reflector 24 may include parabolic shaped IR reflective surface, according to one embodiment, with the IR illumination source 20 located at its focal point. The IR reflector 24 is also generally referred to in the industrial optics field as a "hot mirror" which reflects infrared radiation and passes visible light. The IR reflector 24 is energy transmissive and reflective mirror that reflects substantially all infrared radiation into a substantially collimated forward beam 30 and transmits substantially all visible light therethrough.

The IR reflector 24 may include a relatively thin layer of substrate material and a relatively thin layer of reflective film. The substrate material may include a quartz material, which is sold under the trademark BOROFLOAT®. The reflective film may include a multi-layer dielectric coating. The IR reflector 24 may include a hot mirror, such as Part No. H43842, commercially available from Edmund Industrial Optics of Barrington, N.J. The IR reflector 24 may include any desirable thickness, such as, for example, a thickness of approximately equal to one-tenth of a millimeter, and may include any desirable shape for achieving a desired IR field of view 30. In the embodiment shown, the IR reflector 24 has a parabolic shape.

The IR reflector 24 employs multilayer dielectric coatings to improve the optical efficiency, reduce the thermal load, and reduce the number of necessary components that are required in the illuminator assembly 12. The multilayer dielectric coatings provide a surface that is nearly one hundred percent reflective in the infrared and near-infrared portion of the electromagnetic energy spectrum (i.e., energy having a wavelength in the range of $7\times10^{-7}$-$1\times10^{-3}$ meters) and nearly one hundred percent transmissive in the visible portion of the electromagnetic energy spectrum (i.e., energy having a wavelength in range of $4\times10^{-7}$-$7\times10^{-7}$ meters).

According to one embodiment, the parabolic IR reflector 24 may have a diameter of about twelve centimeters (12 cm), for use in a vehicle headlight application. According to this example, the IR reflector 24 is parabolic shaped, having a radius of curvature of about eighty millimeters (80 mm). In this example, the illuminator assembly 12 has a focal length of about forty millimeters (40 mm) with the IR source 20 considered to be a point source positioned forty millimeters (40 mm) in front of the IR reflector 24. In this embodiment, the IR illumination source 20 and reflector 22 emits IR and visible light radiation into a cone shape and an angle of about one hundred forty degrees to one hundred sixty degrees (140° to 160°), according to one exemplary range. The infrared radiation reflected from the IR reflector 24 is substantially collimated and thus is highly concentrated in a narrow field of view 30 that covers a significantly long range (e.g., one hundred fifty meters (150 m)).

Mounted to the housing 14 and positioned behind the IR reflector 24 is the visible light mirror 26. The visible light mirror 26 collects the visible light passing through IR reflector 24 and reflects and scatters the visible light in a second field of view (beam) 32. The visible light in the second field of view 32 is directed downward at an angle (e.g., fifteen degrees (15°)) towards the roadway, according to the embodiment shown, so as not to blind passengers in oncoming vehicle traffic. The visible light mirror 26 may have an aperture diameter of 18.5 centimeters, according to one embodiment. According to this embodiment, the center of the visible mirror 26 is lower with respect to the center of the IR reflector 24 and is rotated downward about an angle of approximately fifteen degrees (15°), according to one example.

By reflecting and scattering the visible light energy in the second field of view 32 towards the roadway in front of the vehicle 10, oncoming vehicle drivers are not blinded by the visible light illumination. Additionally, the visible light energy is recycled and may be used to supplement the existing vehicle headlamps, thus improving driver visibility in the near field road scene. It should be appreciated that the illuminator assembly 12 may be used as a supplement to or a replacement of the vehicle low beam headlamps to supply both IR and visible light illumination.

The illumination source 20, reflector 22, IR reflector 24 and visible light reflector 26 are mounted in housing 14 and may be secured in place via conventional mounting assembly, such as brackets and fasteners. The housing 14 may include the conventional headlamp assembly of the vehicle 10 or may be separate therefrom. In one embodiment, housing 14 may be located in the conventional vehicle headlamp assembly and packaged with other components and assemblies including, but not limited to, a high beam illuminator assembly and/or low beam illuminator assembly.

Accordingly, the night vision illuminator assembly 12 advantageously provides for an energy efficient and cost affordable illuminator for illuminating infrared radiation in a narrow collimated first beam 30 forward of the vehicle 10 and recycles visible light energy that is reflected and scattered forward of the vehicle 10 in a second beam 32 to supplement the visible light headlamps of the vehicle 10. It should be appreciated that the illuminator assembly 12 may be employed in a night vision system which further employs a video imaging camera to capture images that are illuminated by the infrared illumination 30. It should further be appreciated that the illuminator assembly 12 may be employed in any of a number of applications both onboard the vehicle and off of the vehicle. For example, the illuminator assembly 12 may be employed in a portable night vision system, according to one embodiment.

It will be understood by those who practice the invention and those skilled in the art, that various modifications and improvements may be made to the invention without departing from the spirit of the disclosed concept. The scope of protection afforded is to be determined by the claims and by the breadth of interpretation allowed by law.

The invention claimed is:

1. An infrared illuminator assembly comprising:

a housing;

an illumination source for generating infrared radiation and visible light radiation;

an infrared reflector arranged to receive infrared radiation emitted from the infrared illumination source, wherein the infrared reflector reflects infrared radiation in a first field of view and transmits visible light therethrough;

a visible light reflector located behind the infrared reflector for receiving the visible light transmitted through the infrared reflector, wherein the visible light is reflected from the visible light reflector in a second field of view; and a light source reflector located forward of the illumination source for reflecting infrared radiation and visible light radiation from the illuminator source onto the infrared reflector.

2. The illuminator assembly as defined in claim 1, wherein the infrared radiation reflected from the infrared reflector is substantially collimated.

3. The illuminator assembly as defined in claim 1, wherein the visible light reflected by the visible light reflector is substantially scattered.

4. The illuminator assembly as defined in claim 1, wherein the infrared reflector is substantially a parabolic mirror and the illuminator source is substantially located at a focal point of the infrared reflector.

5. The illuminator assembly as defined in claim 1, wherein the infrared reflector comprises a hot mirror that substantially reflects all infrared radiation and substantially transmits all visible light radiation.

6. The illuminator assembly as defined in claim 1, wherein the assembly is located on a vehicle for providing night vision infrared illumination.

7. The illuminator assembly as defined in claim 6, wherein the infrared illumination is radiated substantially forward of the vehicle parallel to ground, and wherein the visible light reflected from the visible reflector is radiated at an angle towards the ground.

8. The illuminator assembly as defined in claim 1, wherein the infrared reflector comprises a multi-layer dielectric coating on a substrate.

9. The infrared illuminator assembly as defined in claim 1, wherein the infrared radiation has a wavelength in the range of $7\times10^{-7}$–$1\times10^{-3}$ meters, and the visible light has a wavelength in the range of $4\times10^{-7}7\times10^{-7}$ meters.

10. An illuminator assembly for supplying a first beam of infrared radiation and a second beam of visible light radiation, said illuminator assembly comprising:

a housing;

an illumination source for generating infrared radiation and visible light radiation;

an infrared reflector arranged to receive the infrared radiation and visible light radiation generated by the illumination source, wherein the infrared reflector reflects infrared radiation in a first beam and transmits visible light radiation therethrough;

a visible light reflector located behind the infrared reflector for receiving visible light transmitted through the infrared reflector, wherein the visible light is reflected from the visible light reflector in a second beam; and light source reflector located forward of the illumination source for reflecting infrared radiation and visible light radiation from the illuminator source onto the infrared reflector.

11. An illuminator assembly as defined in claim 10, wherein the infrared radiation is reflected from the infrared reflector in a substantially collimated first beam, and wherein the visible light radiation is reflected from the visible light reflector in a substantially non- collimated second beam.

12. The illuminator assembly as defined in claim 10, wherein the infrared reflector is a substantially parabolic mirror and the illuminator source is substantially located at a focal point of the infrared reflector.

13. The illuminator assembly as defined in claim 10, wherein the infrared reflector comprises a hot mirror that substantially reflects all infrared radiation and substantially transmits all visible light radiation.

14. The illuminator assembly as defined in claim 10, wherein the assembly is located on a vehicle for providing night vision illumination.

15. The illuminator assembly as defined in claim 14, wherein the infrared illumination is radiated in the first beam substantially forward of the vehicle parallel to the ground, and wherein the visible light reflected from the visible reflector is radiated in the second beam at an angle towards the ground.

16. The illuminator assembly as defined in claim 10, wherein the infrared reflector comprises a multi-layer dielectric coating on a substrate.

17. A method of illuminating first and second beams infrared radiation and visible light comprising the steps of:

generating infrared radiation and visible light via an illumination source;

directing the infrared radiation and visible light radiation onto an infrared reflector, wherein infrared radiation and visible light emitted forward of the illumination source is reflected via a light source reflector located in front of the illumination source onto the infrared reflector;

reflecting the infrared radiation into a first beam via the infrared reflector;

transmitting visible light through the infrared reflector; and reflecting the visible light via a visible light reflector in a second beam.

18. The method as defined in claim 17, wherein the steps of reflecting infrared radiation and visible light further comprises collimating the infrared radiation in the first beam and scattering the visible light in the second beam.

19. The method as defined in claim 18, wherein the method is employed onboard a vehicle for providing nighttime illumination.

20. The method as defined in claim 17, wherein the first beam is substantially straightforward of the vehicle, and the second beam is directed at an angle towards the ground.

21. A method as defined in claim 17, wherein the light source reflector reflects energy in a field of view angle of about 140° to 160°.

22. The illuminator assembly as defined in claim 1, wherein the light source reflector reflects energy in a field of view angle of about 140° to 160°.

23. The illuminator assembly as defined in claim 10, wherein the light source reflector reflects energy in a field of view angle of about 140° to 160°.

* * * * *